US007459278B1

(12) United States Patent
Terry et al.

(10) Patent No.: US 7,459,278 B1
(45) Date of Patent: Dec. 2, 2008

(54) SYSTEM AND METHOD FOR LARGE SCALE DETECTION OF HAZARDOUS MATERIALS IN THE MAIL OR IN OTHER OBJECTS

(75) Inventors: William S. Terry, Barton, NY (US); John Thaddeus Beckert, Endicott, NY (US); David L. Ii, Owego, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 108 days.

(21) Appl. No.: 11/497,673

(22) Filed: Aug. 1, 2006

Related U.S. Application Data

(62) Division of application No. 10/270,987, filed on Oct. 15, 2002, now Pat. No. 7,105,135.

(60) Provisional application No. 60/330,055, filed on Oct. 16, 2001.

(51) Int. Cl.
*G01N 33/53* (2006.01)
(52) U.S. Cl. .................... 435/7.1; 435/7.2; 435/7.91; 436/43; 436/542
(58) Field of Classification Search ................ 435/7.1, 435/7.2, 7.91; 436/43, 542; 422/63, 62, 422/82.07
See application file for complete search history.

(56) References Cited

U.S. PATENT DOCUMENTS

| | | | |
|---|---|---|---|
| 4,788,704 A | 11/1988 | Donges et al. ................. 378/99 |
| 4,851,687 A | 7/1989 | Ettinger et al. ......... 250/390.04 |
| 5,363,971 A | 11/1994 | Weeks et al. ................. 209/584 |
| 5,480,612 A | 1/1996 | Margalit ...................... 422/61 |
| 5,648,047 A | 7/1997 | Kardish et al. ................ 422/56 |
| 5,768,334 A | 6/1998 | Maitrejean et al. ............ 378/53 |
| 5,838,758 A | 11/1998 | Krug et al. .................... 378/53 |
| 5,891,656 A | 4/1999 | Zarling et al. ............... 435/792 |
| 5,900,067 A | 5/1999 | Jones ............................ 134/1 |
| 6,139,800 A | 10/2000 | Chandler ................. 422/82.08 |
| 6,300,638 B1 | 10/2001 | Groger et al. ............. 250/458.1 |
| 6,303,316 B1 | 10/2001 | Kiel et al. ....................... 435/6 |
| 6,742,703 B2 | 6/2004 | Esakov et al. ................. 232/45 |
| 2001/0015380 A1 | 8/2001 | Good et al. ............ 235/472.02 |
| 2002/0124664 A1 | 9/2002 | Call et al. ................ 73/863.22 |
| 2002/0126008 A1 | 9/2002 | Lopez et al. ................ 340/540 |
| 2003/0222132 A1 | 12/2003 | Esakov et al. ................. 232/30 |

FOREIGN PATENT DOCUMENTS

| | | |
|---|---|---|
| DE | 10150346 | 5/2002 |
| WO | WO 00/63422 | 10/2000 |
| WO | WO 00/66790 | 11/2000 |
| WO | WO 01/66721 | 9/2001 |
| WO | WO 01/85997 | 11/2001 |

OTHER PUBLICATIONS

U.S. Appl. No. 60/330,055, filed Oct. 16, 2001, entitled System for Large Scale Dectection of Hazardous Materials in the Mail or in Other Objects; Applicants: William S. Terry, et al.
Dereniak, E. L., & Crowe, D. G. (1984). *Optical Radiation Detectors*. New York: John Wiley & Sons, Inc.
Press Release dated Oct. 29, 2001 and *Surebeam® Technology*. Retrieved Oct. 30, 2001 from http://www.surebeamcorp.com.
Press Release dated Oct. 27, 2001. Retrieved Oct. 30, 2001 from http://www.usps.com/news/2001/press/pr01_1027titan.htm.
Press Release dated Oct. 25, 2001. Retrieved Oct. 29, 2001 from http://www.tappi.org/index.asp?pid=20062&rc=1&ch=7.
*Packaging and Shipping Guidelines* (n.d.). Retrieved Oct. 29, 2001 from http://diaglab.vet.cornell.edu/issues/sampshp.html.
Tetracore home page, news item and Press Release (dated Dec. 7, 2000). Retrieved Oct. 30, 2001 from http://www.tetracore.com.
U.S. Postal Service Emergency Preparedness Plan for Protecting Postal Employees and Postal Customers from Exposure to Biohazardous Material and for Ensuring Mail Security Against Bioterror Attacks; Mar. 6, 2002; published by USPS.

*Primary Examiner*—Long V. Le
*Assistant Examiner*—Jacob Cheu
(74) *Attorney, Agent, or Firm*—Burns & Levinson LLP; Jacob N. Erlich; Orlando Lopez

(57) ABSTRACT

A system and method that enables early detection of hazardous materials, such as explosives and biological materials, in the early phases of mail handling or processing.

8 Claims, 4 Drawing Sheets

EXPLOSIVE AGENT #1
EXPLOSIVE AGENT #2
BIO AGENT #1
BIO AGENT #2
BIO AGENT #3

SYSTEM AND METHOD FOR LARGE SCALE DETECTION OF HAZARDOUS MATERIALS IN THE MAIL OR IN OTHER OBJECTS

CROSS REFERENCE TO RELATED APPLICATIONS

This application is a division of U.S. patent application Ser. No. 10/270,987, filed on Oct. 15, 2002, and also claims priority of U.S. Provisional Application 60/330,055, entitled "System for Large Scale Detection of Hazardous Materials in the Mail or in Other Objects", filed on Oct. 16, 2001, which is hereby incorporated by reference herein.

BACKGROUND OF THE INVENTION

This invention relates generally to the detection of hazardous material, and, more particularly to the application and sensing of sensitizing agents for early detection of potentially hazardous material associated with mail pieces or the delivery of other objects.

Recently there has been increased awareness of the potential for large-scale introduction of hazardous materials, that is, either explosives or biological organisms to create chaos or to harm an intended set of victims. Awareness to detection of explosives has led to development of reagents that can be used to detect the presence of nitroaromatics, organic nitrates, nitramines, inorganic nitrates, chlorates and bromates based explosives (see U.S. Pat. No. 5,480,612, "Kits for Detecting Explosives", issued to Y. Margalit on Jan. 2, 1996).

Bacterial agents, such as *Bacillus anthracis* and *Closdistrium botilinum*, can be used as biological hazardous materials. Detection methods for bacterial agents have been typically time-consuming using techniques such as florescent antibody staining (FAST) and enzyme linked immunoassay (ELISA). Detection systems have been recently disclosed that involve labeling antibodies with a detectable label where the detectable label utilizes fluorescence, chemiluminescence or chromatic change (see B. L. Mangold et al., international publication WO 01/83561 A2 for International Application No. PCT/US01/13648).

Detection methods have also been recently disclosed in the which the sensor is a polymer which has an alterable property, such as fluorescence or electrical conductivity, and the property is altered by a means of association of the polymer with a moiety including a property quenching element, a tethering element and a ligand or recognition element (see L. Chen et al., international publication WO00/66790 for International Application No. PCT/US00/12423 and see D. G. Whitten et al., international publication WO01/85997 A1 for International Application No. PCT/US01/14702). In this latter method, upon exposure to the biological agent, the agent can bind to the ligand or recognition element causing the moiety (with the bound biological agent) to separate from the polymer thereby un-quenching the alterable property. (The recognition element can be one of, but not restricted to, a chemical ligand, an antibody or antibody fragment, a peptide nucleic acid, or a protein.) Measurement of the alterable property results in detection of the biological agent.

A popular delivery method among the many delivery methods that terrorists or other criminals utilize to deliver such hazardous materials is to utilize the mail to deliver the hazardous material. In so doing, not only is damage incurred by the intended victims, but also by any set of potential victims that may be in a position of handling such objects as the mail during the delivery or distribution process.

As described above, there is currently technology available to law enforcement organizations to detect the presence of both explosive and biological threats. Test kits utilizing the above described materials generally require the gathering of a sample and analyzing offline. To date, however, there is a lack of systems for early detection of such hazardous material in the early phases of mail handling or processing. Systems currently in place do not deal with detection prior to entering into the formal distribution process. Thus, all along the distribution process potential non-intended victims are being subjected to hazardous material carried by, for example, letter or package mail.

There is a need for a system and method for early detection of such hazardous material in the early phases of mail handling or processing. There is also a need for a system and method for early detection of such hazardous material that can be performed while the mail is being processed.

BRIEF SUMMARY OF THE INVENTION

The system and method of this invention enable early detection of such hazardous material such as detection in the early phases of mail handling or processing. The early detection of such hazardous material utilizing the system and method of this invention can be performed while the mail is being processed.

The system of this invention includes two primary elements: an activation sub-system and a sense and analyze sub-system. The sense and analyze sub-system performs the following major functions: illumination and sensing and analysis of the activation results. In one embodiment, the activation sub-system includes a dispensing system and control of the dispensing system by the computer system. In that embodiment, the illumination and sensing functions are performed by at least one radiation source and at least one detector. During operation of the above embodiment of the system of this invention, a mail piece is transported on a conveyor belt and is placed in the region where the dispensing system can deposit sensitizing agents on the mail piece. After deposition of the sensitizing agents on the mail piece, the radiation source illuminates the mail piece. The interaction of the radiation source with the sensitizing agent is detected by the detector. The output of detector is provided to a computer system where computer readable code causes a processor to analyze the detector output obtained from the interaction of the output of the radiation source and the sensitizing agent deposited on the mail piece. If the analysis indicates that the mail piece possibly contains hazardous materials, the computer readable code causes the processor to identify the mail piece as potentially hazardous. The mail piece can then be set aside for further testing.

For a better understanding of the present invention, together with other and further objects thereof, reference is made to the accompanying drawings and detailed description and its scope will be pointed out in the appended claims.

BRIEF DESCRIPTION OF THE SEVERAL VIEWS OF THE DRAWINGS

FIG. 4 is a top view of a mail piece during processing by a method of this invention.

DETAILED DESCRIPTION OF THE INVENTION

A system and method for early detection of such hazardous material in the early phases of mail or delivery package handling or processing are disclosed herein below. The early detection of such hazardous material utilizing the system and method of this invention can be performed while the mail or similar delivered object is being processed.

Although the description below is given in reference to a mail piece, the term "mail piece" as used herein refers to any object in a delivery system. For example, the same description of this invention applies to a package in a delivery system, packages being loaded onto a transport system and other situations where a package would be handled and transported.

Figure 1:
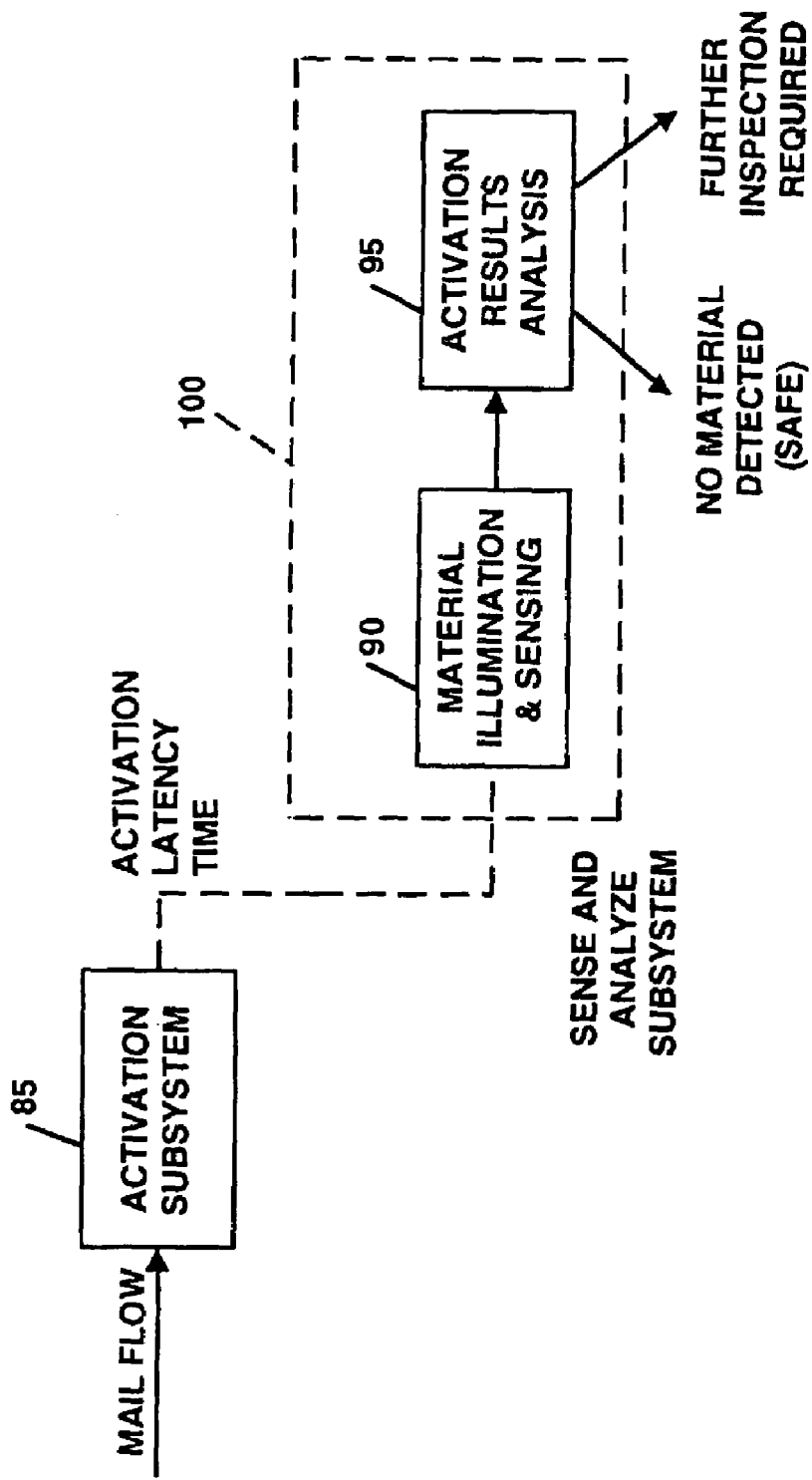
FIG. 1 is a block diagram of an embodiment of the system of this invention.
Figure 2:
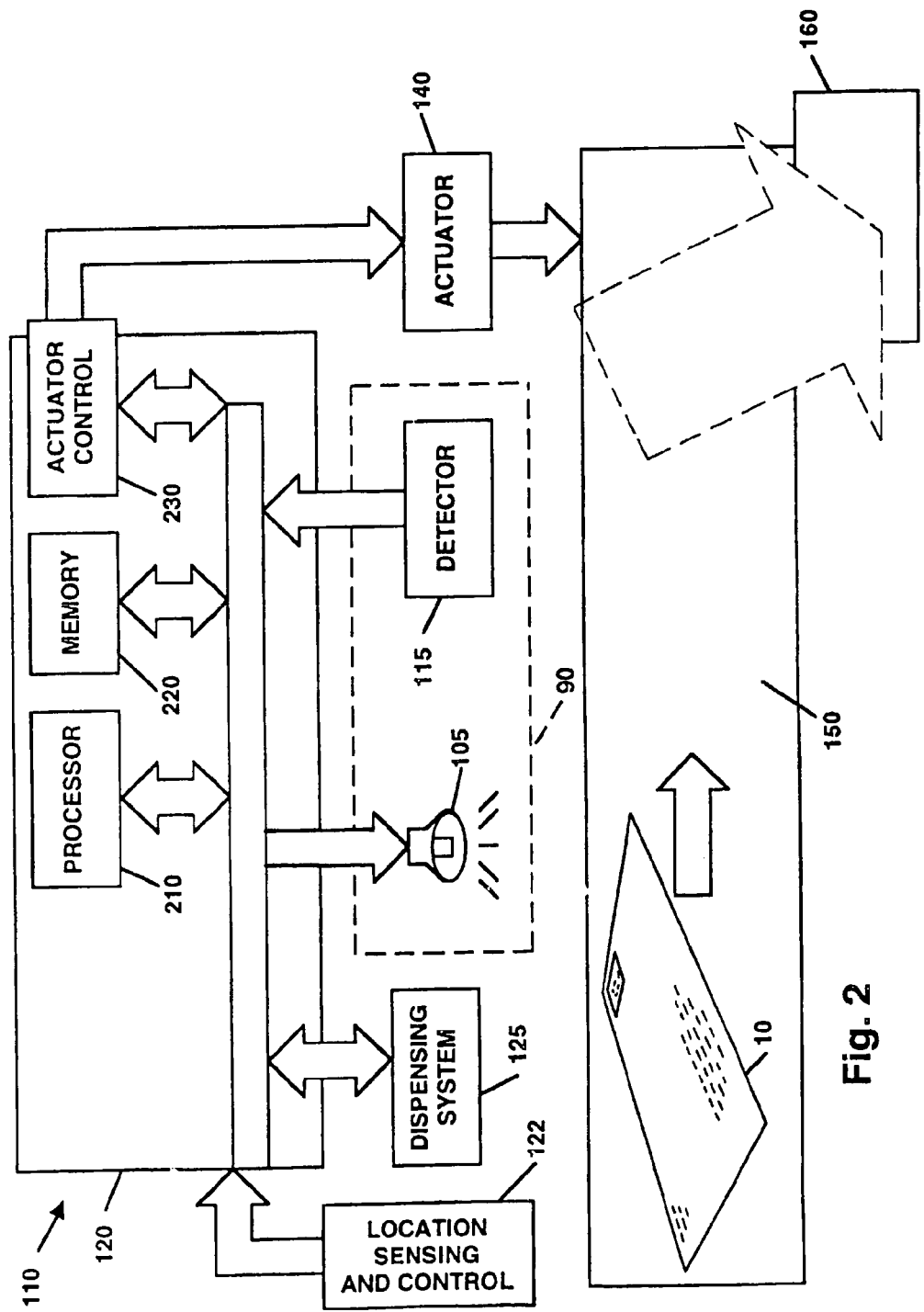
FIG. 2 is a schematic, block representation of an embodiment of the system of this invention.

A block diagram of an embodiment of the system of this invention is shown in FIG. 1 and a schematic, block representation of an embodiment of the system of this invention is shown in FIG. 2.

Referring to FIGS. 1 and 2, the system 110 of this invention includes two primary elements: an activation sub-system 85 and a sense and analyze sub-system 100. The sense and analyze sub-system 100 includes two components: an illumination and sensing component 90 and an activation results analysis component 95. In the embodiment shown in FIG. 2, the activation sub-system 85 of FIG. 1 includes the dispensing system 125 and the control of the dispensing system 125 by means of computer readable code in memory 220 executing in processor 210 of computer system 120. In this embodiment, the illumination and sensing component 90 includes at least one radiation source 105 and at least one detector 115. The radiation source 105 is controlled by computer 120 and the detector 115 provides its output to computer 120. The computer 120 has, in memory 220, computer readable code that causes processor 210 to control the receiving of the output of the detector 115 and to analyze the output of detector 115 when activated mail piece 10 is illuminated by a radiation source 105. The computer 120 also has, in memory 220, computer readable code that causes processor 210 to control the radiation source 105 and the dispensing system 125.

Figure 3:
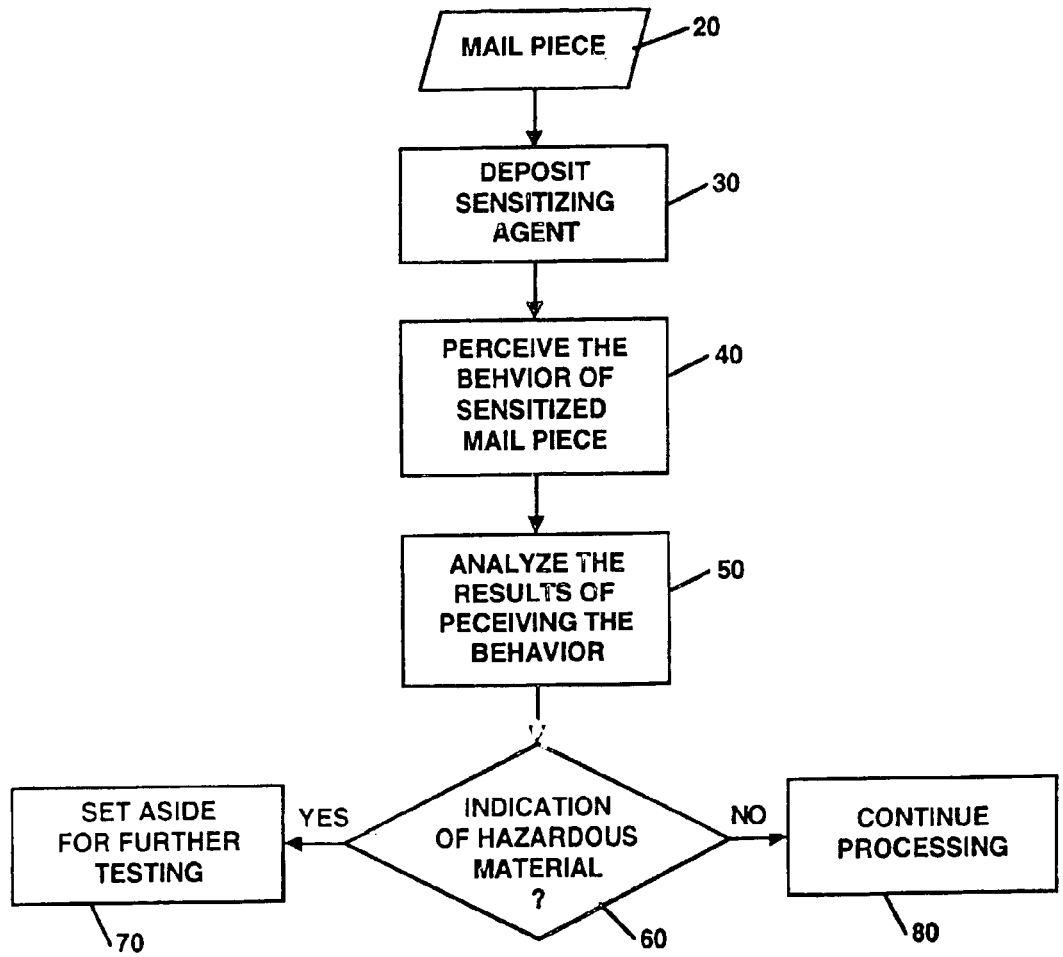
FIG. 3 is a flowchart of an embodiment of the method of this invention.

The operation of the above embodiment of the system of this invention can be best described in reference to FIGS. 2 and 3. Mail piece 10 is transported on conveyor belt 150, or a similar mail transport system, and is placed in the region where dispensing system 125 can deposit sensitizing agents on mail piece 10. For mail processing systems, the transport could be one of several existing transports, for example, the Delivery Bar Code Sorter or Automated Flats Sorting Machine. Transport systems, such as conveyor belts and equivalent transport systems, are known in the art. As the mail piece 10 approaches the dispensing system 125, in one embodiment, a location sensing and control system 122, such as one of the vision systems known in the industrial art, would determine the location and size of the mail piece 10. The location and size information is provided to computer 120 and stored in memory 220. In one embodiment, computer 120 has, in memory 220, computer readable code for receiving the output of the location sensing and control system and for causing the processor 210 to determine the location and size of the mail piece 10.

Dispensing system 125 can have a variety of means for depositing the sensitizing agents. The means required are determined by the medium that carries the sensitizing agent. For example, if the sensitizing agent is one of the reagents described in U.S. Pat. No. 5,480,612, which is incorporated by reference herein, Reagents A, B, and C, described therein, could be deposited using a spray system, a drop dispensing system or an ink jet type nozzle and plunger system. All the above systems can be controlled so that the deposition occurs at a given time and at a desired range or loci of positions. (Known techniques, such as computer vision or digital imaging, use of fiduciary marks, and closed loop control systems can be used to control the deposition.) Control of the dispensing system 125, in one embodiment, occurs via the processor 210 in computer 120 operating under computer code embodied in memory 220. Deposition of Reagent D of U.S. Pat. No. 5,480,612 requires consideration of the acidity of the reagent. (Reagent A of U.S. Pat. No. 5,480,612 is an sensitizing agent for the detection of nitroaromatics such as TNT; reagent B serves the same function for organic esters of nitric acid and nitramines, reagent C serves the same function for inorganic nitrates and reagent D for chlorates or bromates.) Similarly, if the molecules described in international publication WO00/66790 for International Application No. PCT/US00/12423, in international publication WO01/85997 A1 for International Application No. PCT/US01/14702, or in international publication WO01/66721 A2 for International Application No. PCT/US01/07163 (N. Usman et al.) are used in the sensitizing agents, the molecules can be contained in a water-based, a water/DMSO based solution, a gel or clay base. These solutions could be deposited using a spray system, a drop dispensing system or an ink jet type nozzle and plunger system. The clay based or gel based mixtures could be deposited using a wide nozzle and plunger system. In one embodiment, after deposition, the mail piece 10 would appear as shown in FIG. 4, where stripes 310, 320 are obtained by depositing sensitizing agents for the detection of explosives (such as reagents A, B, C, D of U.S. Pat. No. 5,480,612) and stripes 330, 340, 350 are obtained by depositing sensitizing agents for the detection of biological agents (such as solutions or suspensions of the molecules described in international publication WO00/66790, international publication WO01/85997 or international publication WO01/85997 A1).

After deposition, as the mail piece travels along on conveyor belt 150 and, after a travel time equal to or greater than the longest activation latency time for the deposited sensitizing agents has elapsed, the sensitized mail piece 10 approaches illumination and sensing component 90. The speed of the conveyor belt could require modulation or adjustment to accommodate the latency time. As the mail piece 10 approaches the illumination and sensing component 90, in one embodiment, the location sensing and control system 122, such as one of the vision systems known in the industrial art, would determine the location of the mail piece 10 and the location of stripes 310, 320, 330, 340, 350, if necessary.

Still referring to FIG. 2, radiation source 105, under control of computer 120, illuminates the mail piece 10. It should be noted that radiation source 105 can be more than one radiation source and that the radiation source 105 could include, in one embodiment, an optical subsystem (not shown) to focus the beam of radiation. The radiation source 105 emits the radiation in the wavelength range required to activate one of the sensitizing agents deposited by dispensing system 125. In the embodiment in which one of the sensitizing agents is one of the reagents described in U.S. Pat. No. 5,480,612, the required radiation source for that sensitizing agent could be ambient light or a "white" light source. In the embodiment in which one of the sensitizing agents is one of the solutions or suspensions of the molecules described in international publication WO00/66790, international publication WO01/85997 or international publication WO01/85997 A1, where the molecules are designed to detect a biological agent by a change in fluorescence or luminescence, the required radiation source for that sensitizing agent would be a radiation source of a determined wavelength spectrum. The radiation source 105, in that embodiment, would be a laser or a filtered broad wavelength source and, if needed for sensitivity or to avoid interaction with other sensitizing agents, it would be focused by an optical system (not shown). It should be noted that it is possible to select other alterable properties besides those discussed above. The alterable property can also be, but is not limited to, a change in UV absorbance, optical rotation, capacitance, or resistance (see, for example, international publication WO01/66721 A2). The latter alterable properties require different "radiation" sources. Sensing of UV absorbance would require a UV source; sensing of optical rotation would require a radiation source of a predetermined wavelength and polarization; sensing of capacitance or resistance would require a source of radio frequency (RF) radiation.

The interaction of the radiation source 105 with the sensitizing agent in one of the "stripes" 310, 320, 330, 340, or 350 is detected by detector 115. In the embodiment in which one of the sensitizing agents is one of the reagents described in U.S. Pat. No. 5,480,612 and the source of radiation 105 is ambient light or a "white" light source, detector 115 can be one or more CCD or CMOS detectors with color filters. The reagents described in U.S. Pat. No. 5,480,612 exhibit a change in color when exposed to a target explosive material. A CCD or CMOS detector with color filters would enable calorimetric detection. In the embodiment in which one of the sensitizing agents is one of the solutions or suspensions of molecules designed to detect a biological agent by a change in fluorescence or luminescence, and the radiation source 105 is laser or a filtered broad wavelength source, detector 115 can be one of the detectors described in E. L. Dereniak, D. G. Crowe, *Optical Radiation Detectors*, ISBN 0-471-89797-3 (1984, John Wiley & Sons). The detector 115, in this embodiment, includes means for detecting the emitted radiation in a predetermined wavelength band (spectral band). Examples of such means (also referred to as wavelength separating means) are filters, including Liquid Crystal Tunable Filters (LCTF) or Acousto-optic Tunable Filters (AOTF) or a holographic grating or a prism or a polychromator, placed between the emitting mail piece 10 and the photo-detecting component of detector 110. Collecting optics could be used between the wavelength separating means and the emitting surface. If the alterable property of the sensitizing agent is the UV absorbance, optical rotation, capacitance, or resistance, detector 115 would be a w detector, a polarization sensitive optical detector, or an RF detector or antenna, respectively.

The output of detector 115 is provided to computer system 120. Memory 220, a computer usable medium, has computer readable code embodied therein that causes processor 210 to analyze the detector output obtained from the interaction of the output of source 105 and the sensitizing agent deposited on mail piece 10. If the analysis indicates that mail piece 10 appears to contain hazardous materials, the computer readable code causes processor 210 to identify the mail piece 10 as potentially hazardous. The identification can occur through an output device (not shown) such as a video display unit, a printer or an alarm or a combination of these output devices. In one embodiment, if the analysis indicates that mail piece 10 potentially contains hazardous materials, the computer readable code causes processor 210 to send signals to actuator control module 230. Actuator control module 230 causes actuator 140 to select mail piece 10, separate it from the stream of mail pieces and set it aside in area 160 for further inspection.

It should be noted that, although the above discussion of an embodiment of this invention describes the operation of the embodiment with a radiation source 105 and a detector 115, several radiation sources and several detectors would be used to analyze the response of several sensitizing agents for the detection of different hazardous materials.

It should also be noted that the term "mail piece" as used herein refers to any object in a delivery system. The term "radiation source" as used herein applies to any source that provides an output that interacts with a sensitizing agent. "Luminescence" as used herein includes fluorescence.

Each computer readable code within the scope of the claims below may be implemented in any programming language, such as assembly language, machine language, a high-level procedural programming language, or an object-oriented programming language. The programming language may be a compiled or interpreted programming language.

Each computer readable code may be implemented in a computer program product tangibly embodied in a computer-readable storage device for execution by a computer processor. Method steps of the invention may be performed by a computer processor executing a program tangibly embodied on a computer-readable medium to perform functions of the invention by operating on input and generating output.

Common forms of computer-readable or usable media include, for example, a floppy disk, a flexible disk, hard disk, magnetic tape, or any other magnetic medium, a CDROM, any other optical medium, punched cards, paper tape, any other physical medium with patterns of holes, a RAM, a PROM, and EPROM, a FLASH-EPROM, any other memory chip or cartridge, a carrier wave, or any other medium from which a computer can read.

Although the invention has been described with respect to various embodiments, it should be realized this invention is also capable of a wide variety of further and other embodiments within the spirit and scope of the appended claims.

What is claimed is:

1. A method for detection of hazardous materials in a mail piece during mail handling or processing, said method comprising the steps of:

transporting the mail piece on a transport system;

depositing at least one sensitizing agent on a surface of the mail piece while the mail piece is being transported;

transporting said mail piece for a predetermined travel time, said predetermined travel time being equal to or greater than an activation latency time for said at leas one deposited sensitizing agent on the mail piece, in order to allow activation prior to reaching sensing means for said at least one sensitizing agent;

sensing, while the mail piece is being transported, said at least one sensitizing agent after being deposited on the mail piece to determine whether hazardous material is located on the surface of the mail piece;

analyzing results of the sensing to determine whether the mail piece possibly contains hazardous materials, wherein a change in a property of the sensitizing agent is indicative of the presence of the hazardous materials; and identifying the mail piece as potentially hazardous, if said analysis indicates that the mail piece possibly contains hazardous materials.

2. The method of claim 1 further comprising:

performing, if the mail piece is identified as potentially hazardous, the further steps of:

culling the mail piece; and, setting the mail piece aside for further inspection.

3. The method of claim 1 wherein said step of depositing comprises applying the sensitizing agent in the form of a solution.

4. The method of claim 1 wherein said step of depositing comprises applying the sensitizing agent in the form of a gel based agent.

5. The method of claim 1 wherein said at least one sensitizing agent is a polymer having an alterable luminescence and wherein exposure to a target biological material results in a detectable change in luminescence.

6. The method of claim 5 wherein said step of sensing comprises the steps of:

exposing the mail piece to radiation at a first spectrum; and, detecting emitted radiation at a second spectrum.

7. The method of claim 1 wherein said at least one sensitizing agent is a reagent and wherein said reagent exhibits a change in color when exposed to a target explosive material.

8. The method of claim 7 wherein said step of sensing comprises utilizing a detector capable of detecting calorimetric change.

* * * * *